United States Patent
Horn et al.

(10) Patent No.: US 10,400,233 B2
(45) Date of Patent: Sep. 3, 2019

(54) HIGH LOAD ENZYME IMMOBILIZATION BY CROSSLINKING

(71) Applicant: Roche Diabetes Care, Inc., Indianapolis, IN (US)

(72) Inventors: Carina Horn, Biblis (DE); Susanne Gawenda, Birkenau (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 240 days.

(21) Appl. No.: 15/232,915

(22) Filed: Aug. 10, 2016

(65) Prior Publication Data

US 2017/0159039 A1    Jun. 8, 2017

Related U.S. Application Data

(63) Continuation of application No. PCT/EP2015/056732, filed on Mar. 27, 2015.

(30) Foreign Application Priority Data

Mar. 31, 2014 (EP) ..................... 14162678

(51) Int. Cl.
| | | |
|---|---|---|
| *A61K 38/00* | (2006.01) | |
| *A61K 38/04* | (2006.01) | |
| *C12N 11/06* | (2006.01) | |
| *C12N 9/04* | (2006.01) | |
| *C12N 9/96* | (2006.01) | |
| *C12Q 1/00* | (2006.01) | |
| *C12Q 1/32* | (2006.01) | |
| *C12N 11/08* | (2006.01) | |
| *C12Q 1/54* | (2006.01) | |

(52) U.S. Cl.
CPC ............ *C12N 11/06* (2013.01); *C12N 9/0006* (2013.01); *C12N 9/96* (2013.01); *C12N 11/08* (2013.01); *C12Q 1/001* (2013.01); *C12Q 1/32* (2013.01); *C12Q 1/54* (2013.01); *C12Y 101/01047* (2013.01); *G01N 2333/904* (2013.01)

(58) Field of Classification Search
CPC ............ A61B 5/14865; A61B 5/14532; A61B 5/14546
See application file for complete search history.

(56) References Cited

U.S. PATENT DOCUMENTS

| | | |
|---|---|---|
| 4,919,770 A | 4/1990 | Preidel et al. |
| 5,108,564 A | 4/1992 | Szuminsky et al. |
| 6,054,039 A | 4/2000 | Shieh |
| 7,547,535 B2 | 6/2009 | Kratzsch et al. |
| 2005/0023152 A1 | 2/2005 | Surridge et al. |
| 2009/0198117 A1 | 8/2009 | Cooper et al. |
| 2017/0311859 A1* | 11/2017 | Hughes .............. A61B 5/14865 |

FOREIGN PATENT DOCUMENTS

| | | |
|---|---|---|
| EP | 0654079 B1 | 7/1993 |
| EP | 0821234 A2 | 1/1998 |
| EP | 1035921 A1 | 12/1998 |
| EP | 0974303 B2 | 1/2000 |
| EP | 1035919 A1 | 9/2000 |
| EP | 1035920 B1 | 7/2002 |
| EP | 1566637 A1 | 8/2005 |
| EP | 1593434 A2 | 11/2005 |
| EP | 1780288 A1 | 5/2007 |
| EP | 1457572 31 | 3/2009 |
| JP | 2000262281 A | 9/2000 |
| WO | 9312418 A2 | 12/1992 |
| WO | 2004113910 A1 | 12/2004 |
| WO | 2005045016 A2 | 5/2005 |
| WO | 2006027222 A1 | 3/2006 |
| WO | 2007012494 A1 | 2/2007 |
| WO | 2007017562 A1 | 6/2007 |
| WO | 2009103540 A1 | 8/2009 |
| WO | 2014001382 A1 | 1/2014 |

OTHER PUBLICATIONS

Nanocs Catalog, Apr. 2001, pp. 1-2.*
Baik Sang-Ho et al., Cooperative Effect of Two Surface Amino Acid Mutations (Q252L and, American Society for Microbiology, Jun. 2005, p. 3285-3293, vol. 71, No. 6.

(Continued)

*Primary Examiner* — Maryam Monshipouri (57) ABSTRACT

Methods of cross-linking polypeptide molecules are provided, where such methods include combining a cross-linking agent and polypeptide molecules in a solution under conditions suitable for a cross-linking reaction to occur. Also provided are preparations of cross-linked polypeptide molecules, where the polypeptide molecules are cross-linked by essentially unbranched cross-linking groups of at least 40 contiguous atoms. Further provided are test chemistry matrices and methods of making the same, where the matrices include a redox cofactor, an agent capable of eliciting a change in at least one measurable property of an indicator reagent in the presence of redox equivalents, an indicator reagent, and a preparation of cross-linked polypeptide molecules as described herein. Test elements and methods of using the same to diagnose diseases such as diabetes also are provided, where the test elements include a test chemistry matrix as described herein.

13 Claims, 5 Drawing Sheets

(56) References Cited

OTHER PUBLICATIONS

Mateo et al.; A New Mild Cross-Linking Methodology to Prepare Cross-Linked Enzyme Aggregates; Laboratory of Biocatalysis and Organic Chemistry; Jun. 3, 2003; www.interscience.wiley.com; 2004 Wiley Periodicals, Inc. —.

Sheldon Roger A., Enzyme Immobilization: The Quest for Optimum Performance, Wiley-VCH Verlag GmbH&Co. KGaA, Feb. 5, 2007, 1289-1307, 349, Weinheim.

Vazquez-Figueroa, Javier et al, Development of a Thermostable Glucose Dehydrogenase by a Structure-Guided Consensus Concept. ChemBioChem. 2007. pp. 2295-2301. 8.

Chen F. et al., Understanding chemical reactivity for homo- and heterobifunctional protein cross-linking agents, Journal of Mass Spectrometry, Apr. 23, 2013, pp. 807-812, vol. 48, No. 7, Wiley Online Library, WO.

Hoenes, Joachim et al., The Technology Behind Glucose Meters: Test Strips, Diabetes Technology & Therapeutics, 2008, pp. S-10-S-26, vol. 10, Supplement 1.

Kazan D. et al, Stabilization of *Escherichia coil* penicillin G acylase against thermal inactivation by cross-linking with dextran dialdehyde polymers, Appl Microbial Biotechnol, Jan. 1, 1997, pp. 191-197, vol. 48, No. 2, Springer-Verlag, WO.

Nadithe V. et al., Synthesis and characterization of hemoglobin conjugates with antioxidant enzymes via poly ( ethylene glycol) cross-linker (Hb-SOD-CAT) for protection from free radical stress, International Journal of Biological Macromolecules, Dec. 1, 2010, pp. 603-613, vol. 47, No. 5, Elsevier, WO.

International Search Report and Written Opinion; PCT/EP2015/056732; dated Dec. 5, 2015.

Guisan Jose M., Immobilization of Enzymes and Cells, Methods in Biotechnology, 2006, Second Edition, Humana Press: [attached in 3 parts].

* cited by examiner

HIGH LOAD ENZYME IMMOBILIZATION BY CROSSLINKING

CROSS-REFERENCE TO RELATED APPLICATIONS

This patent application is a continuation of Int'l Patent Application No. PCT/EP2015/056732 (filed 27 Mar. 2015), which claims priority to and the benefit of EP Patent Application No. 14162678.8 (filed 31 Mar. 2014). Each patent application is incorporated herein by reference as if set forth in its entirety.

TECHNICAL FIELD

This patent application relates generally to chemistry and medicine/medical diagnostics, and more particularly, it relates to methods of cross-linking polypeptide molecules, where the polypeptide molecules are cross-linked by essentially unbranched cross-linking groups having at least forty contiguous atoms. This patent application also relates to preparations including the cross-linked polypeptide molecules, test chemistry matrices including the preparations, and test elements including the test chemistry matrices, as well as methods of making and using the same.

BACKGROUND

Enzyme immobilization has been investigated under the aspects of enabling recycling of enzymes used in chemical synthesis, of convenience of handling (e.g., separation from the product), and of enhanced stability of immobilized enzyme preparations. See, e.g., Sheldon (2007) *Adv. Synth. Catal.* 349:1289-1307. Accordingly, several methods of immobilizing enzymes have been described in the art, including coupling of enzymes to solid particles, crosslinking enzymes, encapsidizing enzymes, and immobilizing enzymes in solid matrices. See, e.g., *Methods in Biotechnology: Immobilization of Enzymes and Cells* (Jose M. Guisan ed., Humana Press $2^{nd}$ ed. 2006). For cross-linking, enzymes can be crystallized, and then cross-linked to produce cross-linked enzyme crystals (CLECs). Alternatively, enzymes can be precipitated, and the precipitates can be treated to produce cross-linked enzyme aggregates (CLEAs®; see, Sheldon (2007), supra). As a crosslinking agent, glutaraldehyde is generally the agent of choice. However, glutaraldehyde has a disadvantage that many enzymes are inactivated during cross-linking, which is attributed to the small size of glutaraldehyde molecules and which is thought to penetrate into protein molecules and thereby inactivate amino acids crucial for enzyme activity (see, id.). Accordingly, dextran polyaldehyde was proposed as alternative cross-linking agent, with improvements as compared to glutaraldehyde shown for nitrilases and penicillin G acylase. See Mateo et al. (2004) *Biotech. Bioeng.* 86:273-276.

Diagnostic test elements usually are manufactured for use in near-patient applications. Therefore, test elements must be robust with respect to handling and storing. This applies, in particular, to the test chemistry of the test elements. See, e.g., Hones et al. (2008) *Diabetes Technol. Ther.* 10:S10-S26.

Many diagnostic test elements, however, are based upon rather complex enzyme test chemistries present on the test elements. In particular, test elements can include a carrier and a detection layer, where the detection layer usually contains enzymes. It is decisive for proper functioning of the test elements that the enzymes remain biologically active during storing and upon treating. Since calibration for an individual measurement is usually not possible, the test elements are normally calibrated batch-wise. The calibration information for a batch of test elements is then stored and used for each test element of the batch regardless of individual differences in treating and storing.

However, pretreatments of diagnostic test elements and storage conditions can severely affect enzyme activity. For example, heat treatment, either during manufacturing or during storing of the test elements, can denature the enzymes so that the overall enzymatic activity of a test element is significantly reduced that, in turn, will result in erroneous test results when such a test element is used. Similarly, with increasing water content in the detection layer, enzymes and other components of the detection layer will tend to diffuse, which is a particular problem in test elements having more than one layer of test chemistry. This problem is particularly pronounced in applications where test elements are exposed to environmental conditions for an extended time such as, for example, in "open vial" applications or where test elements are provided in cartridges. Accordingly, enzymes used in such test elements have been absorbed to charged particles such as Transpafil. However, using charged particles for immobilization has the disadvantage of severely diluting the specific activity of the enzyme immobilized, as calculated on a per mass basis, which, in turn, necessitates an increase of layer thickness to provide the required enzyme activity per area. This increase in layer thickness, however, usually leads to increased reaction times due to slowed diffusion of the analyte into the layer, meaning that increased test times are required.

Accordingly, there is a need for means and methods of improving immobilization of polypeptide molecules. In particular, methods of immobilizing enzymes avoiding strong dilution of the specific activity per mass and/or for immobilizing enzymes in the form of finely dispersible aggregates are needed.

BRIEF SUMMARY

The problems as described above can be solved by means and methods with the features of the independent claims. Exemplary embodiments, which might be realized in an isolated fashion or in any arbitrary combination, are listed in the dependent claims.

Accordingly, the present patent application provides methods of cross-linking polypeptide molecules, where the methods can include the step of:

a. combining at least one cross-linking agent and polypeptide molecules in a solution under conditions suitable for a cross-linking reaction to occur.

In the methods, the combining step can be achieved by dropwise addition of the cross-linking agent to the solution including the polypeptide molecules. In some instances, the combining step occurs under agitation. In other instances, the cross-linking agent is dissolved in a compatible organic solvent and then added to the solution including the polypeptide molecules, where the compatible organic solvent can be dimethylsulfoxide (DMSO).

In the methods, the cross-linking agent can include a contiguous chain of at least forty (40) atoms. In some instances, the cross-linking agent has a molecular mass of about 0.6 kDa to about 20 kDa, of about 0.9 kDa to about 10 kDa, of about 1 kDa to about 5 kDa, or even about 3 kDa. In other instances, the cross-linking agent is an unbranched molecule chemically activated at both ends. In certain instances, the cross-linking agent can be a polyethylene glycol (PEG) such as bis-activated PEG or bis-N-hydroxysuccinimide-activated PEG (O,O'-bis[2-(N-succinimidylsuccinylamino)ethyl] PEG; NHS-PEG).

In the methods, the polypeptide molecules include at least about 5 amino acids interconnected via peptide bonds, at least about 25 amino acids interconnected via peptide bonds; or even at least about 100 amino acids interconnected via peptide bonds. Moreover, the amino acids can be alpha-amino acids, especially L-alpha-amino acids. In some instances, the polypeptide molecules can be an enzyme such as a dehydrogenase. In certain instances, at least a fraction of the polypeptide molecules are dehydrogenase molecules, where at least about 80% of the polypeptide molecules are dehydrogenase molecules or where at least about 90% of the polypeptide molecules are dehydrogenase molecules. In certain instances, the dehydrogenase is a glucose dehydrogenase (GlucDH) or a mutant GlucDH such as GlucDH E170K/Q252L.

In some instances, the polypeptide molecules can be synthesized by in vitro peptide synthesis (i.e., chemical synthesis). In other instances, the polypeptide molecules can be synthesized by in vitro protein biosynthesis by, for example, a living cell. The methods therefore generally relate to in vitro methods.

In some instances, the polypeptide molecules are present in the solution at an initial concentration of about 0.1 mM to about 5 mM, of about 0.3 mM to about 4 mM, or even of about 1.5 to about 3.5 mM.

In the methods, the molar ratio of cross-linking agent: polypeptide molecules is from about 0.2 to about 5, from about 0.5 to about 4, from about 0.8 to about 3, or even from about 1 to about 2.

In the methods, the solution has a pH of about 7 to about 9, of about 7.5 to about 8.8, of about 7.3 to about 9.3, or even about 8.3.

The methods can include steps in addition to above-mentioned steps. For example, further steps may relate to purifying the polypeptide molecules prior to cross-linking and/or removing surplus reagents and/or unwanted side products after the cross-linking. Furthermore, one or more steps may be performed by automated equipment.

Also provided herein are methods of producing test chemistry matrices, where the methods can include the steps of:
a. obtaining a preparation of cross-linked polypeptide molecules as described herein, where the polypeptide molecules are an enzyme; and
b. producing a test chemistry matrix by admixing a redox cofactor, an agent capable of eliciting a change in at least one measurable property of an indicator reagent in the presence of redox equivalents, an indicator reagent, and the preparation of cross-linked polypeptide molecules.

In some instances, the redox cofactor, the agent capable of eliciting a change in at least one measurable property of an indicator reagent, and/or the indicator agent are one compound (i.e., the same compound).

The methods can include steps in addition to above-mentioned steps. Furthermore, one or more steps may be performed by automated equipment.

Also provided herein are methods of manufacturing diagnostic test elements, where the methods can include the step of:
a. applying/generating/providing a test chemistry matrix as described herein on a carrier.

The methods can include steps in addition to above-mentioned step. Furthermore, one or more steps may be performed by automated equipment.

In view of the above, cross-linked polypeptides are provided that include the polypeptide molecules cross-linked by essentially unbranched cross-linking groups including at least 40 contiguous atoms. In some instances, the polypeptide molecules are an enzyme such as GlucDH, especially GlucDH E170K/Q252L. In some instances, the cross-linking groups are PEG chains.

Preparations also are provided that include the cross-linked polypeptides as described herein. The preparations can be used in diagnosing diseases such as diabetes.

Moreover, test chemistry matrices are provided that include a redox cofactor, an agent capable of eliciting a change in at least one measurable property of an indicator reagent in the presence of redox equivalents, an indicator reagent, and cross-linked polypeptide molecules as described herein.

In some instances, the redox cofactor, the agent capable of eliciting a change in at least one measurable property of an indicator reagent, and/or the indicator agent are the same compound.

In some instances, the cross-linked polypeptide molecules are an enzyme such as GlucDH, especially GlucDH E170K/Q252L.

Furthermore, diagnostic test elements are provided that include a test chemistry matrix as described herein applied/generated/provided on a carrier. In some instances, at least a part of the test chemistry matrix is incorporated in a test field. In some instances, the diagnostic test elements are in a form of a test strip or a test band. In certain instances, the diagnostic test elements are included in a cartridge.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 4A specifically shows free GlucDH2, and FIG. 4B shows cross-linked GlucDH2. In FIG. 4A, both the first layer 128, into which the labelled enzyme was originally included, and the second layer 130, into which the labeled enzyme has diffused, are visible. In FIG. 4B, only the first layer, into which the labelled enzyme was originally incorporated, is visible.

FIG. 5A shows free GlucDH2; and FIG. 5B shows cross-linked GlucDH2.

FIG. 6A specifically shows dry and warm conditions, and FIG. 6B specifically shows moist and warm conditions. X-axis: incubation time (days); Y-axis: residual activity ($A_{rel}$) relative to time=0 days (%).

FIG. 7A specifically shows storage under dry and warm conditions, and FIG. 7B specifically shows storage under moist and warm conditions. X-axis: incubation time (days); Y-axis: percent mobility (%).

Corresponding reference characters indicate corresponding parts throughout the several views of the drawings.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY
EMBODIMENTS

The compositions, diagnostic test elements and methods now will be described more fully hereinafter with reference to the accompanying drawings, in which some, but not all embodiments of the inventive concept are shown. Indeed, the compositions, test elements and methods may be embodied in many different forms and should not be construed as limited to the embodiments set forth herein; rather, these embodiments are provided so that this disclosure will satisfy applicable legal requirements.

Likewise, many modifications and other embodiments of the compositions, diagnostic test elements and methods described herein will come to mind to one of skill in the art to which the disclosure pertains having the benefit of the teachings presented in the foregoing descriptions and the associated drawings. Therefore, it is to be understood that the compositions, test elements and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the compositions, diagnostic test elements and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

Advantageously, and unexpectedly, the work described in this patent application shows that polypeptide molecules can be efficiently cross-linked in solutions (i.e., without precipitating the polypeptide molecules). The methods described herein find particular use with polypeptide molecules such as enzymes that often times are inactivated by precipitation and find use with polypeptides that are difficult to re-dissolve after precipitation. Moreover, the work in this patent application shows that cross-linked polypeptide molecules obtained via the methods described herein are especially well suited for producing test chemistry matrices, since the cross-linked polypeptide molecules are on the one hand large enough to drastically decrease diffusion through the matrix layer or layers, and on the other hand are small enough for fine dispersion of the polypeptide molecules over the chemistry matrices. Furthermore, the work in this patent application shows that by cross-linking enzymes via the methods described herein, the dilution of specific activity, which is a consequence of cross-linking with high-molecular weight polymers, can be drastically reduced.

As used herein, "analyte" means a chemical compound present in a body fluid. The analyte can be a small molecule (i.e., the analyte is not a biological macromolecule). In some instances, the analyte is an organic molecule, especially an organic molecule capable of undergoing a redox reaction in the presence of the test chemistry matrices described herein. In other instances, the analyte can be a molecule of a individual's metabolism. Alternatively, the analyte can be a low molecular weight chemical compound such as, for example, a chemical compound with a molecular mass of less than 1000 u (1000 Da; $1.66 \times 10^{-24}$ kg).

As used herein, "body fluid" means all bodily fluids of a subject having or suspected of having the analyte. Example of body fluids include, but are not limited to, plasma, serum, lacrimal fluid, urine, lymph, cerebrospinal fluid, bile, stool, sweat, and saliva. In some instances, the body fluid is blood. Sample thus can relate to any sub-portion of a body fluid removed from a subject prior to applying the body fluid sample to a test element. Samples can be obtained by well-known techniques including, for example, venous or arterial puncture, epidermal puncture, and the like.

Examples of analytes include, but are not limited to, ethanol, ascorbic acid, cholesterol, glycerol, urea, 3-hydroxybutyrate, lactate, pyruvate, triglycerides, ketones, liver parameters, creatinine, and HDL. In specific instances, the analyte is blood glucose and the actual concentration to be determined is at least about 10 mg/dL, at least about 50 mg/dL, at least about 60 mg/dL, at least about 70 mg/dL, at least about 80 mg/dL, at least 90 about mg/dL, at least about 100 mg/dL, at least about 110 mg/dL, at least about 120 mg/dL, at least about 130 mg/dL, at least about 140 mg/dL, or at least about 150 mg/dL. Preferably, the analyte is glucose and the concentration to be determined is in the range of about 0 mg/dL to about 800 mg/dL, about 10 mg/dL to 600 mg/dL, or even about 50 mg/a to about 300 mg/dL.

As used herein, "about" means within a statistically meaningful range of a value or values including, but not limited to, a stated concentration, length, width, height, angle, weight, molecular mass, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

The compositions and diagnostic test elements find particular use in detecting and diagnosing various diseases such as, for example, diabetes.

As used herein, "diagnosis" or "diagnosing" means assessing a probability according to which an individual is suffering or will suffer from a disease or condition referred to in this patent application. One of skill in the art understands that such an assessment is usually not intended to be correct for 100% of the individuals to be diagnosed. Diagnosis, however, requires that a statistically significant portion of the individuals can be correctly diagnosed to suffer from the disease or condition. Whether a portion is statistically significant can be determined without further ado by one of skill in the art using various well-known statistic evaluation tools (e.g., determining confidence intervals, p-value, Student's t-test. Mann-Whitney test, etc.). Details are found in, for example, Dowdy & Wearden, Statistics for Research (John Wiley & Sons, New York 1983). Exemplary confidence intervals can be at least about 90%, at least about 95%, at least about 97%, at least about 98%, or even at least about 99%. Likewise, exemplary p-values can be 0.1, 0.05, 0.01, 0.005, or 0.0001. The probability envisaged herein allows that the diagnosis will be correct for at least about 60%, at least about 70%, at least about 80%, or even at least about 90% of the individuals of a given cohort or population.

As used herein, the term "disease" relates to any clinically relevant deviation from normal metabolism. Accordingly, "diagnosis of disease" relates to determining at least one clinically relevant parameter and/or emergency parameter of an analyte, including, without limitation, malate, ethanol, ascorbic acid, cholesterol, glycerol, urea, 3-hydroxybutyrate, lactate, pyruvate, triglycerides, ketones, liver parameters, creatinine, HDL, and the like and evaluating whether a clinically relevant deviation from normal metabolism is present. One of skill in the art understands that diagnosis includes determining an absence of the analyte (i.e., diagnosis by exclusion).

Compositions

Cross-linked polypeptide molecules, preparations thereof, and test chemistry matrices including the same are provided herein. As used herein, "polypeptide" or "polypeptides" mean a chemical molecule comprising a plurality of peptide bonds such as, for example, peptide bonds formed between amino acids.

The polypeptides can be without catalytic activity of their own such as, for example, a cellular receptor, an immunoglobulin, or a part thereof. Alternatively, the polypeptides can have catalytic activity (i.e., the polypeptides are an enzyme). One of skill in the art understands that purity of a polypeptide preparation is generally less than 100%. Accordingly, at least a fraction of the polypeptide molecules are molecules having the respective enzymatic activity such as, for example, at least about 80% or at least about 90% of the polypeptide molecules are molecules having the respective enzymatic activity.

With respect to the cross-linking agent, it can include a contiguous chain of at least 40 atoms. As used herein, "cross-linking agent" means a chemical molecule including reactive chemical groups forming a covalent bond with the polypeptide molecules to be cross-linked under the appropriate conditions. In some instances, the cross-linking agent includes a contiguous chain of at least about 40 atoms, of at least about 50 atoms, or even of about at least 65 atoms. In some instances, the cross-linking agent includes at least two reactive chemical groups. In other instances, the cross-linking agent has exactly two reactive chemical groups. One of skill in the art understands that at least two of the reactive chemical groups can be arranged spatially in such a way to enable the two reactive chemical groups to contact two different polypeptide molecules to be cross-linked.

As used herein "reactive chemical group" means a chemical group reacting with a group of atoms, such as an amino acid side chain present in a polypeptide, and thereby forming a covalent bond under appropriate conditions. The reactive chemical group can be a chemical group reacting with a group of atoms present in a polypeptide under conditions not causing denaturation of the polypeptide. In some instances, the conditions not causing denaturation are physiological conditions including, but not limited to, about 25° C., 100 kPa in an appropriate solvent. Examples of reactive chemical groups include, but are not limited to, cyanate esters, epoxides, isocyanates, imidates, thioimidates, and N-hydroxy-succinimide groups.

Moreover, the cross-linking agent has a molecular mass of about 0.6 kDa to about 20 kDa, of about 0.9 kDa to about 10 kDa, of about 1 kDa to about 5 kDa, of even about 3 kDa. In some instances, the cross-linking agent is an unbranched molecule chemically activated at both ends. Examples of cross-linking agents include, but are not limited to PEGs such as bis-activated PEG or NHS-PEG.

With respect to the polypeptide molecules, they can be an enzyme such as a dehydrogenase or oxidoreductase. As used herein "dehydrogenase," means an enzyme that is capable of catalyzing oxidation or reduction of a substrate by transferring hydrides ($H^-$) in a one-step-mechanism or $H^+/e^-$ in a two-step mechanism as redox equivalents to or from its redox cofactor as referred to herein elsewhere. Stated differently, a dehydrogenase is a polypeptide that is capable of catalyzing oxidation of a substrate by transferring hydrides ($H^-$) as redox equivalents to an acceptor molecule such as a redox cofactor as referred to herein elsewhere.

Dehydrogenases for use here typically are those that depend on a redox cofactor (or sometimes referred to as co-enzyme) such as pyrrolo quinoline quinone (PQQ), nicotinamide-adenine-dinucleotide (NAD) or a derivative thereof, or a flavine cofactor such as flavin-adenine-dinucleotide (FAD) or flavine mononucleotide (FMN). Examples of dehydrogenases include, but are not limited to, lactate dehydrogenase (EC number 1.1.1.27 or 1.1.1.28), glucose dehydrogenases (see below), alcohol dehydrogenase (EC number EC number 1.1.1.1 or 1.1.1.2), L-amino acid dehydrogenase (EC number 1.4.1.5), glycerin dehydrogenase (EC number 1.1.1.6), malate dehydrogenase (EC number 1.1.1.37), 3-hydroxybutyrate dehydrogenase (EC number 1.1.1.30), sorbitol dehydrogenase (EC number 1.1.1.14), or cholesterol dehydrogenase.

In some instances, the dehydrogenase is a glucose dehydrogenase (GlucDH) especially glucose dehydrogenase (EC number 1.1.1.47), quinoprotein glucose dehydrogenase (EC number 1.1.5.2) such as PQQ-dependent glucose dehydrogenase (EC number 1.1.5.2), glucose-6-phospate dehydrogenase (EC number 1.1.1.49), NAD-dependent glucose dehydrogenase (EC number 1.1.1.119), and FAD-dependent glucose dehydrogenase (EC number 1.1.99.10), as well as enzymatically active mutants thereof.

Enzymatically active mutants of enzymes can be obtained by substituting, adding or deleting one or more amino acids from the amino acid sequences reported for the aforementioned wild type enzymes. Example of such enzymatically active mutant enzymes include, but are not limited to PQQ-dependent GlucDH mutants having an improved substrate specificity when compared to wild type counterparts as disclosed in, for example, U.S. Pat. Nos. 7,132,270 or 7,547,535. Further enzymatically active mutant enzymes are those disclosed in, for example, Baik et al. (2005) *Appl. Environ. Microbiol.* 71:3285-3293, Vásquez-Figueroa et al. (2007) *ChemBioChem* 8:2295-2301, and Int'l Patent Application Publication No. WO 2005/045016. In some instances, the enzymatically active mutant enzyme is a glucose dehydrogenase (E.C. 1.1.1.47) mutant as disclosed in Int'l Patent Application Publication No. WO 2009/103540A1 (see, e.g., p. 21) or EP Patent No. 1,660,648 having a mutation at least at amino acid positions 96, 170 and/or 252. Examples of specific mutations envisaged at these amino acid positions include, but are not limited to, Glu96Gly, Glu170Arg or Lys, and/or Lys252Leu, especially the combination Glu170Lys/Lys252Leu. In certain instances, the mutations are Glu170Arg and Gln252Leu in GlucDH from *Bacillus subtilis* ("GlucDH E170K/Q252L," also referred to herein as "GlucDH").

The cross-linked polypeptide molecules therefore can include polypeptide molecules cross-linked by essentially unbranched cross-linking groups having at least 40 contiguous atoms. In some instances, the cross-linking groups are PEG chains. In some instances, the cross-linked polypeptide molecules are included in aggregates. In certain instances, the polypeptide molecules are an enzyme such as GlucDH, especially GlucDH E170K/Q252L.

In addition to the cross-linked polypeptide molecules, preparations including the same are provided herein, where the cross-linked polypeptide molecules are cross-linked by unbranched side chains having at least 40 contiguous atoms. Alternatively or additionally, the cross-linked polypeptides in the preparation are included in covalent aggregates having on average about 5 to about 50 polypeptide molecules, from about 10 to about 40 polypeptide molecules, or even from about 15 to about 25 polypeptide molecules. For example, in the case of a polypeptide with a molecular mass of $1\times10^2$ kDa, the cross-linked polypeptide molecules are in covalent aggregates with an apparent molecular mass of about $5\times10^2$ kDa to about $5\times10^3$ kDa, of about $1\times10^3$ kDa to about $4\times10^3$ kDa, or even of $1.5\times10^3$ kDa to about $2.5\times10^3$ kDa.

The specific activity per mass of the preparations can be at least about 50% of the specific activity of the polypeptide molecules before cross-linking, at least about 60% of the specific activity of the polypeptide molecules before cross-linking, or even at least about 70% of the specific activity of the polypeptide molecules before cross-linking.

In addition to preparations of cross-linked polypeptides, test chemistry matrixes are provided herein, where the test chemistry matrixes include a redox cofactor, an agent capable of eliciting a change in at least one measurable property of an indicator reagent in the presence of redox equivalents, an indicator reagent, and cross-linked enzymes and/or cross-linked polypeptide molecules as described herein.

As used herein, "matrix" or "matrices" mean a mixture including various compounds/components as specified herein. One of skill in the art understands that the matrices may include additional components such as, for example, buffer components (e.g., phosphate buffered saline, Tris buffer, citrate buffer, glycerine phosphate buffer, or Good's buffer) or other salts, detergents, or the like, including components as specified herein below. One of skill in the art also understands that the matrices described herein may be an inhomogeneous mixture (i.e., a dispersion or mixture).

In some instances, the matrices can be a dry composition. As used herein, "dry composition" means that the composition is essentially free of a solvent or a mixture of solvents. As used herein, "essentially free" means that at least about 85%, at least about 90%, at least about 92%, at least about 95%, at least about 98%, or at least about 99% of the solvent or solvent mixture originally present in a solution or dispersion of the composition has been removed therefrom. Accordingly, it is contemplated that the solvent or solvent mixture is present in the dry composition in an amount of up to about 5%, up to about 2%, up to about 1%, or even less than 1%. Alternatively, a dry composition is a composition having water in an amount of up to about 5%, up to about 2%, up to about 1%, or even less than 1%. Methods for determining residual water are known in the art such as, for example, determining residual water in a composition using a phosphorus pentoxide sensor as described in Int'l Patent Application Publication No, WO 1993/012418. The aforementioned percentage values and the other percentage values referred herein used to define amounts refer to percent by weight (w/w), if not otherwise noted. Thus, the matrices herein can be a solid composition under normal conditions (i.e., under room temperature and normal pressure).

As used herein, "test chemistry matrix" or "test chemistry matrices" means a matrix of compounds including at least the redox cofactor, the reagent capable of eliciting a change in at least one measurable property of an indicator reagent in the presence of redox equivalents; the indicator reagent, and the cross-linked enzyme, the cross-linked polypeptide molecules and/or the preparation of cross-linked polypeptide molecules as described herein. Various possibilities of designing test chemistry matrices are known in the art. In this regard, reference may be made to the above-mentioned prior art documents. Specifically, reference may be made to Hones et al. (2008), supra. However, other types of test chemistry matrices are possible. Exemplary compositions of test chemistry matrices are described elsewhere herein and shown herein in the examples.

In particular instances, the test chemistry matrices include more than one type of cross-linked enzyme and/or more than one preparation of cross-linked polypeptide molecules as described herein. For example, the test chemistry matrices can include a glucose dehydrogenase cross-linked as described herein and a diaphorase cross-linked as described herein, where the two enzymes were cross-linked in separate cross-linking reactions.

In some instances, the test chemistry matrices described herein are adapted to change at least one measurable property in the presence of an analyte of interest. As used herein, "measurable property" means any property of the test chemistry that changes in the presence of the analyte and that can be transferred into a physical signal of any kind. The change of the measurable property and/or the signal generatable therefrom are proportional to the analyte concentration in the sample. For example, the measurable property can be a redox state of at least one of the components of the test chemistry matrices such as the redox cofactor and/or the redox mediator. Accordingly, the detection reaction can be a redox reaction. In certain instances, the detection reaction produces redox equivalents and/or electrons as intermediates and/or products. In certain instances, the measurable property is the concentration of a reduced or an oxidized redox mediator as described herein (i.e., the measurable property is the redox state of the mediator in the test chemistry).

Methods of converting the measurable property as defined above into a physical signal that can be read as a measurement value are well known in the art and are described in, for example, EP Patent Application Publication Nos. 0,821,234 and 0,974,303, as well as US Patent Application Publication No. 2005/0023152. As such, the measurable property can be a property of a compound of the test chemistry matrices different from a mediator and/or indicator reagent; accordingly, in such case the mediator and/or indicator reagent can be omitted from the test chemistry matrices. As a non-limiting example, enzymatic reduction of NAD or a derivative thereof may be detected by UV-irradiation. Accordingly, the redox cofactor, the mediator and the indicator agent may be the same compound.

In some instances, the measurable property is an electrochemical property. Accordingly, the test chemistry matrices can be an electrochemical test chemistry matrix contacting at least two electrodes. Suitable electrodes, electrode setups, suitable further compounds of electrochemical test chemistry matrices and modes of operation of the same are known and are described in, for example, Int'l Patent Application Publication Nos. WO 2007/071562, WO 2009/0198117, WO 2007/071562, WO 2014/001382, and references cited therein. Examples of electrode configurations are described in, for example, Int'l Patent Application Publication Nos. WO 2004/113910 and WO 2006/027222. It is contemplated that electrochemical test chemistry matrices include one or more chemical reagents for reacting with the analyte to produce an electrochemical signal that represents the presence of the analyte in the sample. Electrochemical properties include amperometric or coulometric responses indicative of the concentration of the analyte. See, e.g., U.S. Pat. Nos. 4,919,770; 5,108,564; and 6,054,039.

Alternatively, the measurable property is an optical property. Accordingly, the test chemistry matrices perform at least one optically detectable detection reaction in the presence of the analyte. Specifically, the optically detectable signal produced by the detection reaction is proportional to the amount and/or to the concentration of the analyte in the sample. The measurable property therefore can be a change in color and/or color intensity of the test chemistry (i.e., a change in the absorption and/or emission spectrum of the test chemistry). Thus, in the change of the measurable property, the optical property can be a reflection property such as a reflectance and/or a remission, a transmission property such as an absorption, a color, and a luminescence such as a fluorescence.

As used herein, "detecting" or "detection" means quantifying an amount of an analyte present in a sample such as a body fluid sample (i.e., measuring the amount or concentration of the analyte semi-quantitatively or quantitatively). The detecting can be accomplished by a variety of methods known in the art or detailed herein below. Thus, the detecting the amount of the analyte can be achieved by all known means for detecting the amount of the analyte in the sample, provided that they are adapted to specifically detect the analyte and are compatible with the requirements the compositions and methods herein.

As used herein, "amount" means an absolute amount of the analyte, a relative amount or concentration of the analyte, as well as any value or parameter that correlates thereto. Such values or parameters include intensity signal values from all specific physical or chemical properties obtained from the analyte referred to herein by measurements. One of skill in the art understands that values correlating to the aforementioned amounts or parameters can also be obtained by all standard mathematical operations.

As noted above, one component of the test chemistry matrices is the redox factor. As used herein, "redox cofactor" means a molecule that can serve as an acceptor for enzymatically transferred redox equivalents and, in particular, hydride ($H^-$). In some instances, the redox cofactor can be PQQ, NAD or FAD. One of skill in the art understands that the redox cofactor to be included depends on the properties of the dehydrogenase. For example, PQQ can be combined with a PQQ-dependent glucose dehydrogenase, NAD can be combined with a NAD-dependent glucose dehydrogenase, and FAD can be combined with a FAD-dependent glucose dehydrogenase. The redox cofactor alternatively can be a derivative of PQQ, NAD or FAD. Examples of redox cofactor derivatives of NAD are described in, for example, Int'l Patent Application Publication No. WO 2007/012494, with respect to the NAD/NADH and/or NADP/NADPH derivatives therein. In certain instances, the redox cofactor is carbaNAD as described in, for example, Int'l Patent Application Publication No. WO 2007/012494.

Another component of the test chemistry matrices is the agent capable of eliciting a change in at least one measurable property of an indicator reagent in the presence of redox equivalents. As used herein, "agent capable of eliciting a change in at least one measurable property of an indicator reagent in the presence of redox equivalents" means a molecule that, in the presence of redox equivalents, is capable of inducing a change in at least one measurable property in the indicator reagent. One of skill in the art understands that the agent also may elicit a change in more than one measurable property of the indicator reagent, which may then subsequently be detected. Furthermore, the agent also may elicit a change in measurable properties of more than one indicator reagent which may then subsequently be detected.

The agent thus is capable of transferring directly or indirectly (i.e., via a further mediator) redox equivalents from the redox cofactor to the indicator reagent. As a consequence of the transfer of the redox equivalents, the indicator reagent will be modified so that a change in at least one measurable property occurs. When the measurable property is an optical property, it can be a color-less or non-fluorescing indicator reagent in an oxidized state converted into a colored or fluorescent indicator reagent by the transfer of redox equivalents mediated by the agent in a reduced state. The transfer of the redox equivalents may be direct in that the redox equivalents are transferred by the agent to the indicator reagent or may be indirect. In the latter case, the redox equivalents are transferred from the agent to an intermediate mediator that subsequently transfers the redox equivalents to the indicator reagent.

More than one mediator can be used. For example, the agent may transfer the redox equivalents to a first mediator, which subsequently transfers the redox equivalents to a second mediator, where the second mediator then transfers the redox equivalents to the indicator reagent. Thus, a mediator cascade of more than two mediators can be used. An advantage of using one or more mediators for transferring redox equivalents to the indicator reagent is that the timing of the detection of the measurable property can be improved.

Mediators are well known in the art and include, for example, potassium ferricyanide, quinone derivatives, Nile blue (CAS no.: 3625-57-8), Meldola's blue (CAS no.: 7057-57-0), osmium complexes as described in EP Patent No. 1,457,572, transition metal complexes such as ruthenium hexamine chloride, or nitroso-aniline-derivatives.

Examples of agents include, but are not limited to, phenazines such as phenazinethosulfate, phenazinmethosulfate, 1-(3-carboxypropoxy)-5-ethylphenaziniumtrifluoromethansulfonate and 1-methoxyphenazine-methosulfate. Such phenazines can be applied for eliciting a change in at least one optical property of an indicator reagent. Details on such phenazines can be found in, for example, EP Patent Application Publication No. 0,654,079. Alternatively or additionally, the agent can be a chinone such as phenanthrenchinone, phenanthrolinchinone or benzo[h]-chinolinchinone. Alternatively still, the agent can be a nitrosoaniline such as nitrosoaniline is [(4-nitrosophenyl)imino] dimethanol-hydrochloride. In some instances, the nitrosoaniline is 4-bis(hydroxyethyl)-1-nitroso-aniline or 4-bis(hydroxyethyl)-3-methoxy-1-nitrosoaniline. Alternatively still, the agent can be an enzyme capable of catalyzing the transfer of redox equivalents from the redox cofactor to the indicator reagent, such as diaphorase.

Another component of the test chemistry matrices is the indicator reagent. As used herein, "indicator reagent" means a compound changing at least one measurable (i.e., optical) property dependent on activity of the cross-linked polypeptide molecules described herein, especially cross-linked enzyme. In some instances, the indicator reagent is an optical indicator substance, which performs at least one optically detectable property change when at least one of the enzymes or when the enzyme comprised in the test chemistry matrix reacts with the analyte. Thus, the at least one indicator reagent can be one or more dyes performing a change in an optical property indicative of the enzymatic reaction of the at least one enzyme and the analyte.

The optical property of the indicator reagent changes dependent on the activity of the enzyme. Thus, the change of the optical property only occurs if the enzyme catalyzes the detection reaction, where the change of optical property is proportional to the number of catalytic cycles undergone by the enzyme present in the test chemistry matrix. Moreover, the change of optical property is proportional to the number of analyte molecules converted by the enzyme.

In some instances, the optical property changing in the indicator reagent is measurable in the test chemistry matrix having the indicator reagent. Thus, the at least one optical property may be any property of the test chemistry matrix that changes in the presence of the analyte and which can be transferred into an optical signal of any kind. Typically, the change of the optical property and/or the signal generatable therefrom are proportional to the analyte concentration in the sample. Additionally or alternatively, a predetermined or determinable relationship between the optical property, the change of the optical property and/or the signal generatable therefrom and the concentration of the analyte in the sample may exist, which may be used for deriving the concentration from the signal.

One of skill in the art understands that the measurable property of the test chemistry matrices also may be a property of a compound different from the mediator and/or the indicator reagent and that, in such case, the mediator and/or indicator reagent can be omitted from the test chemistry matrices (e.g., enzymatic reduction of NAD or a derivative thereof may be detected by UV-irradiation). Accordingly, the redox cofactor, the mediator, and the indicator agent may be the same compound.

Another component of the test chemistry matrices is the cross-linked enzyme, the cross-linked polypeptide molecules, and/or the preparation of cross-linked polypeptide molecules as described herein.

Diagnostic Test Elements

Diagnostic test elements are provided herein for determining an analyte concentration (or amount) in a body fluid, where the test elements include a test chemistry matrix as described herein applied/generated/provided on a surface of a carrier.

As used herein, "carrier" means a solid support onto which one or more of the test chemistry matrices herein can be applied. In particular, the test chemistry matrix can be immobilized on a surface of the carrier. Moreover, the test chemistry matrix can be spatially arranged on the carrier. Thus, the carrier must be arranged in a manner to allow for detecting the change of the at least one measurable property of the indicator reagent (i.e. it does not include components or a spatial arrangement that would interfere with the detecting the at least one measurable property). Suitable carriers may include vials containing test elements such as, for example, vials arranged in a well-plate format. Other assays may apply optical waveguides or semiconductor plates. Known carriers, however, are those conventionally used for test elements, which typically have one or more layers forming a solid carrier.

In some instances, the diagnostic test elements include a test field containing the test chemistry matrix, where the test field has a sample application side onto which the body fluid sample is applied and a detection side that allows for detection of a change in a measurable property when the analyte reacts with the components of the test chemistry matrix. The sample is to be applied to the sample application side, and it is contemplated that cells, such as erythrocytes present in blood samples, do not reach the detection side. Details on such a diagnostic test element and the manufacture thereof are described in, for example, EP Patent No. 0,821,234. Further details on diagnostic test elements and the manufacture thereof are described in EP Patent Nos. 1,035,919 and 1,035,920.

The test field can include a transparent foil onto which one or more than one film layer is applied. The film layers can be produced from dispersions or emulsions of polymeric film formers that contain microscopic polymer particles that are insoluble in the carrier liquid (usually water) and are finely dispersed in the carrier liquid. If the carrier liquid is removed by evaporation during film formation, then the particles come closer and finely touch one another. The large forces that occur in this process and the gain in surface energy that accompanies film formation results in the particles growing into a substantially closed film layer. Alternatively, it is possible to use an emulsion of the film former dissolved in a solvent. The dissolved polymer is emulsified in a carrier liquid that is immiscible with the solvent. Examples of suitable polymers for film formers include, but are not limited to, polyvinyl esters, polyvinyl acetates, polyacrylic esters, polymethacrylic acid, polyacrylamides, polyamides and polystyrene. In addition to homopolymers, mixed polymerizates are suitable such as, for example, butadiene, styrene or maleic acid ester.

One or more of the layers also can include a swelling agent. By adding a swelling agent that swells well (i.e., a substance that increases its volume when it takes up water), one obtain layers that not only can be penetrated relatively rapidly by sample liquid but also can have good cell and blood pigment separation properties despite this opening effect of the swelling agent. The swelling properties should be so good that for a test in which the change of the at least one measurable property is mainly dependent on the penetration of the sample liquid through the layer, the change of the measurable property is measurable after a maximum of one minute. Examples of suitable swelling agents include, but are not limited to, methyl vinyl ether maleic acid anhydride copolymer, xanthan gum, and methyl vinyl ether maleic acid copolymer.

Single layer layouts of diagnostic test elements are known in the art. See, e.g., EP Patent Application Publication Nos. 1,566,637 and 1,780,288. Likewise, two-layer layouts are known in the art and include a first and a second film layer resting on top of one another in this order. It is important that the first layer located on the transparent foil scatters light considerably less than the overlying second layer. The non-coated side of the transparent foil is referred to as the detection side and the side of the second layer that is opposite to the side to which the second layer rests on the first layer is referred to as the sample application side. The two so-called film layers are located on a transparent foil in the test field of the diagnostic test carrier. For this, plastic foils come into consideration, which are impermeable to liquid. Polycarbonate foil has proven to be particularly suitable. The two film layers can be produced from coating compounds that contain the same polymeric film formers, or they can be produced from coating compounds that contain different polymeric film formers. Whereas the first layer contains a swelling agent and optionally a weakly light scattering filler, the second layer requires a swelling agent and in any case at least one pigment that scatters light strongly. In addition, the second layer can contain non-porous fillers as well as porous fillers.

In the case of a single-layer film, which may be used in electrochemical detection, the cross-linked polypeptide molecules herein can be incorporated into the single layer. In the case of multi-layer layouts, however, the cross-linked polypeptide molecules can be incorporated into in one film layer (i.e., the first film layer).

To optimize the test field in the diagnostic test elements, it has proven to be particularly advantageous when all film layers contain a non-hemolyzing wetting agent. Neutral (i.e., non-charged) wetting agents can be used such as, for example, N-octanoyl-N-methyl glucamide.

To produce a two-layer test field in the diagnostic test elements, the respective film layers each are produced successively from a homogeneous dispersion of the components. For this, the transparent foil is used as a base to form the coating compound for the first film layer. After the coating compound for the first film layer has been applied with a particular layer thickness, the layer is dried. Afterwards, the coating compound for the second layer is applied to this layer also with a thin layer thickness and dried. The test field produced in this manner can be mounted on a supporting layer for better handling, those materials coming into consideration for such a layer, which do not take up the liquid to be examined. These are so-called non-absorptive materials. Examples include plastic foils made of, for example, polystyrene, polyvinyl chloride, polyester, polycarbonate or polyimide. Metal foils or glass are suitable as further supporting materials.

In some instances, the detection side of the test field that is to be observed and measured for a change in at least one optical property of the indicator reagent should be visible through the supporting layer to determine the analyte to be detected in the body sample. This can be achieved by a transparent supporting layer. However, it is also possible that the supporting layer has a perforation that is covered by the detection side of the test field. The detection side is then visible through the perforation. In other instances, there is a hole in the supporting layer below the detection side of the test field through which the detection side of the test field can be observed. The hole has a somewhat smaller diameter than the smallest linear dimension of the test field so that the test field outside the hole rests on the supporting layer and can be attached there.

In some embodiments, the test elements include a capillary canal. Such a layout is known in the art as described in, for example, EP Patent Application Publication No. 1,035, 921. In some embodiments, the test elements can be produced from a test element band as described in, for example, EP Patent Application Publication No. 1,593,434, or is a test strip. Moreover, the test elements can be included in a cartridge, where the cartridge has a multitude of diagnostic test elements.

Methods

Methods of cross-linking polypeptides are provided herein that include the step of combining at least one cross-linking agent and polypeptide molecules in a solution under conditions suitable for a cross-linking reaction to occur.

The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

As used herein, "in a solution" or "in solution" mean a state of a chemical compound being present in a liquid in a homogenous mixture, the chemical compound (i.e., the solute) being dissolved in the liquid (i.e., the solvent).

Accordingly, solvents for use herein are solvents that do not cause the polypeptides herein to denature and/or to precipitate. One of skill in the art understands how to select an appropriate solvent for a given polypeptide (e.g., short polypeptides can be dissolved in polar organic solvents such as DMSO; whereas, longer polypeptides, especially those having more than 50 amino acids, can be dissolved in aqueous solutions). Thus, the solution can be an aqueous solution, especially a buffered solution having a pH of about 7 to about 9, of about 7.3 to about 9.3, of about 7.5 to about 8.8, or even about 8.3. In some instances, the buffers do not react with the reactive chemical group of the cross-linking agent. In specific instances, the buffer is sodium and/or potassium phosphate buffer, such as, for example, 0.1 M potassium-phosphate-buffer. One of skill in the art understands that a specific polypeptide may require additional components in the solvent to stay in solution (e.g., mono- and/or divalent cations, cofactors, a substrate or substrates, and/or detergents).

As used herein, "cross-linking" means covalently interconnecting two polypeptide molecules via an intervening cross-linking group. In principle, it is possible with the methods described herein to cross-link non-identical types of polypeptide molecules (mixed cross-link) to thereby cross-link enzymes molecules catalyzing different steps of a chemical reaction sequence. As a non-limiting example, a glucose dehydrogenase and a diaphorase may be combined in a cross-linking reaction as described herein. One of skill in the art understands that mixed cross-links are not in principle limited to two non-identical types of polypeptide molecules, but may contain more than two types of polypeptide molecules. In most instances, however, polypeptide molecules of the same molecular species are cross-linked.

In the methods, the combining step can be achieved by dropwise addition of the cross-linking agent to a solution including the polypeptide molecules. In some instances, the combining step occurs under agitation. Alternatively, the cross-linking agent can be dissolved in a compatible organic solvent and then added dropwise to the solution including the polypeptide molecules. The compatible organic solvent should be selected so as to not react with the cross-linking agent, to not inactivate or denature the polypeptide molecules at the final concentration present in the mixture, and to dissolve the cross-linking agent. Typically, the organic solvent is water-free and can be DMSO, especially water-free DMSO.

One of skill in the art understands that "conditions suitable for a cross-linking reaction to occur" depends on the cross-linking agent and in particular on the chemically reactive groups therein, as well as on the specific type of polypeptide molecules, and knows to select conditions accordingly. Exemplary conditions are described below in the Examples. In some instances, however, the polypeptide molecules can be present in the solution at an initial concentration of about 0.1 mM to about 5 mM, of about 0.3 mM to about 4 mM, or even of about 1.5 mM to about 3.5 mM. Moreover, the molar ratio of crosslinking agent:polypeptide molecules is about 0.2 to about 5, about 0.5 to about 4, about 0.8 to about 3, or even about 1 to about 2.

With respect to the cross-linking agent, it can include a contiguous chain of at least 40 atoms, of at least about 50 atoms, or even of about at least 65 atoms. Moreover, the cross-linking agent has a molecular mass of about 0.6 kDa to about 20 kDa, of about 0.9 kDa to about 10 kDa, of about 1 kDa to about 5 kDa, of even about 3 kDa. In some instances, the cross-linking agent is an unbranched molecule chemically activated at both ends. In certain instances, the cross-linking agent can be bis-activated PEG or NHS-PEG.

With respect to the polypeptide molecules, they can include at least about 5 amino acids interconnected via peptide bonds, at least about 25 amino acids interconnected via peptide bonds; or even at least about 100 amino acids interconnected via peptide bonds. Moreover, the amino acids can be alpha-amino acids, especially L-alpha-amino acids. In some instances, the polypeptide molecules can be an enzyme such as a dehydrogenase. In certain instances, at least a fraction of the polypeptide molecules are dehydrogenase molecules, where at least about 80% of the polypeptide molecules are dehydrogenase molecules or at least about 90% of the polypeptide molecules are dehydrogenase molecules. In particular instances, the dehydrogenase is a GlucDH or a mutant GlucDH such as GlucDH E170K/Q252.

In addition to methods of cross-linking polypeptide molecules, methods of making test chemistry matrices also are provided, where the methods include the steps of:

a. obtaining a preparation of cross-linked enzyme molecules as described herein and/or cross-linked polypeptide molecules as described herein; and b. producing a test chemistry matric by admixing a redox cofactor, an agent capable of eliciting a change in at least one measurable property of an indicator reagent in the presence of redox equivalents, an indicator reagent, and the preparation of cross-linked enzyme molecules or cross-linked polypeptide molecules.

The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

Also provided herein are methods of manufacturing diagnostic test elements, where the methods can include the step of:

a. applying/generating/providing a test chemistry matrix as described herein on a surface of a carrier to produce a diagnostic test element.

The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

EXAMPLES

The inventive concept will be more fully understood upon consideration of the following non-limiting examples, which are offered for purposes of illustration, not limitation.

Example 1

Methods and Results:

In a first attempt to cross-link GlucDH2, short-chain, bis-expoxy- and bis-NHS-activated PEGs were used, using the following ratios: 0.3 mM GlucDH2 (in a 10 mg/ml protein solution) in reaction with a tenfold excess of bis-NHS-activated PEGs or a 50-fold excess of bis-expoxy-activated PEG.

Reactions were performed in 0.1 molar K-phosphate buffer at pH 7.5, adding the activated PEGs dropwise at room temperature under stirring.

Reactions with bis-expoxy-activated PEG led to a complete loss of activity of GlucDH2 at low molecular masses (380 and 520 g/mol), whereas with an intermediate molecular mass (980 g/mol) 85% of the activity could be preserved.

Figure 1:
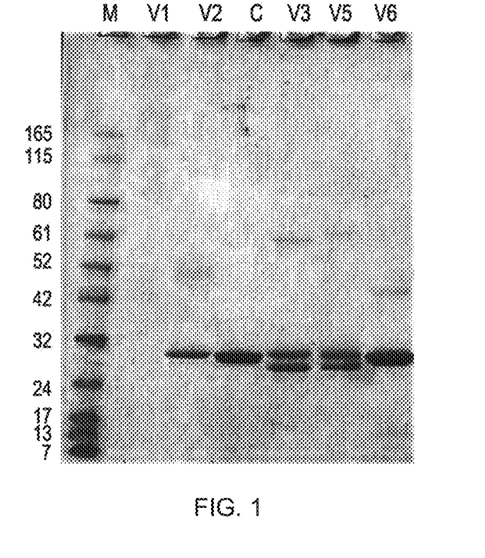
FIG. 1 shows a SDS-gel-chromatographic analysis of cross-linking polypeptide molecules as specified in Table 1 below (acrylamide concentration in the gel of about 4% to about 12%); amphiblue staining of the mutant glucose dehydrogenase, GlucDH E170K/Q252L (GlucDH2). M: marker; C: control; lanes V1-V6 correspond to experiments V1-V6 of Table 1. Lane V1 showed no free GlucDH2. Lanes V1 and V2 were cross-linked with NHS-PEG; whereas lanes V3 and V5-V6 were cross-linked with expoxy-PEG. The molecular weight of marker compounds is indicated in kDa.

This experiment shows which lowest molecular mass is required for an activated linker to prevent the essential lysine residue in GlucDH2 from reacting, which would lead to a complete inactivation of the enzyme. However, no high-molecular weight protein aggregates could be obtained by cross-linking with expoxy-activated PEG (FIG. 1). In contrast, NHS-activated PEGs with molecular masses of 3,000 and 10,000 g/mol showed preservation of activity as well as cross-linking (Table 1, FIGS. 1-2). The products of cross-linking with 3,000 g/mol Bis-NHS-activated PEG were analyzed by gel permeation chromatography, using a superose 6-column. It was found that the conditions indicated above mainly led to PEGylation instead of cross-link.

TABLE 1

| Experiment | Crosslinker (structure) | Mol Wt PEG (g/mol) | Residual activity (%) | Results |
|---|---|---|---|---|
| V1 | [structure] | 3000 | 61% | cross-linked and active enzyme, no monomers |
| V2 | [structure] | 10000 | 90% | cross-linked and active enzyme, small amounts of monomers |
| V3 | [structure] | 380 | 1% | inactive enzyme, no cross-link |
| V5 | [structure] | 526 | 9% | inactive enzyme, no cross-link |
| V6 | [structure] | 980 | 85% | active enzyme, no cross-link |

Example 2

Methods and Results:

To optimize cross-linking, the amount of protein was drastically increased to thereby increase intermolecular reaction. The pH value also was increased to improve the reactivity of amino groups comprised in the enzyme towards NHS-groups. Moreover, NHS-activated PEGs were dissolved in dimethylsulfoxide (DMSO) to avoid premature hydrolysis of the NHS group.

Accordingly, the following improved reaction conditions were used: 2.85 mM GlucDH2 (80 mg/ml protein solution) reacting with 0.5-to 2-fold excess of bis-NHS-activated PEG (3,000 g/mol). Cross-link was performed in 0.2 molar sodium-bicarbonate buffer at pH 8.3 adding NHS-activated PEG dissolved in DMSO by slow dropping at room temperature while stirring the reaction mixture. The resulting, viscous solution was dialyzed against 0.05 M potassium/sodium phosphate buffer pH 7.0. Activity was determined by an activity assay and the size of the products was determined by gel permeation chromatography.

Figure 2:
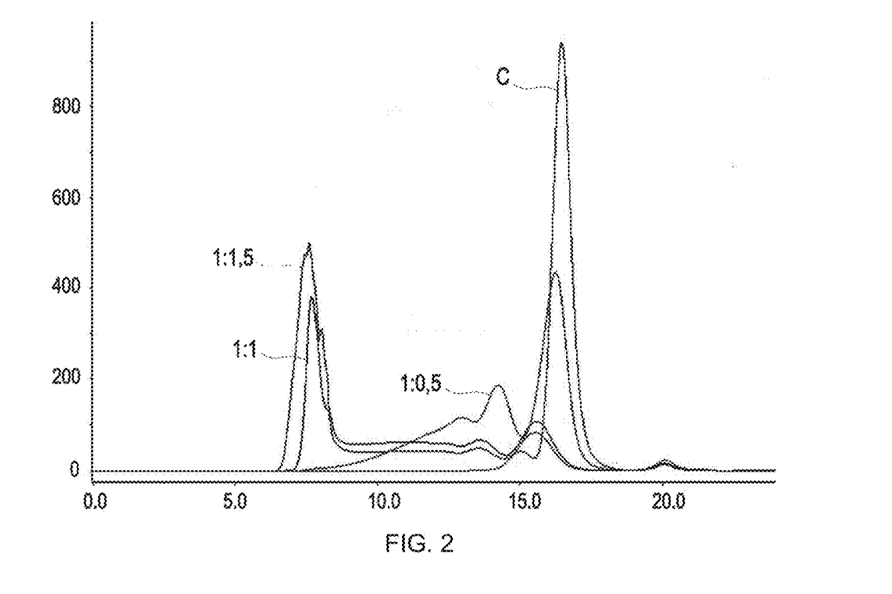
FIG. 2 shows gel permeation chromatography of reaction products of Example 2. Reaction products were chromatographed on a superpose 6 10/300 column with a mobile phase of 150 mM potassium phosphate buffer/150 mM NaCl, pH 7.0, at a flow rate of 0.5 ml/min and were detected in a flow cell at 280 nm. The amount of sample was 1.25 mg of protein in each case. X-axis: elution volume (ml); Y-axis: absorbance at 280 nm (arbitrary units).

As shown in FIG. 2, starting from a molar ratio of enzyme:PEG of 1:1, no free GlucDH2 was observed; increasing the molar ratio to 1:1.5, the proportion of large cross-linking products increased.

The cross-linked enzyme produced in Example 2 was included into a first layer of a two-layer glucose test element and was evaluated regarding stability and mobility of the enzyme. As shown in Table 2, an increase of the molar ratio of enzyme:PEG leads to the production of larger cross-linking products. The molecular weight of GlucDH2 thus produced, as determined by gel permeation chromatography, increases from 112 kDa (free enzyme) up to 2,000 kDa when a molar ratio of 1:1.5 is used. Correspondingly, the mobility of the enzyme in the test element strongly decreases with increasing size of the cross-link product. Stability in the test element was tested at 35° C. and 85% relative humidity and was not significantly different as compared to free GlucDH2.

TABLE 2

|  | Molar Ratio | | | | |
| --- | --- | --- | --- | --- | --- |
|  | 1:0 | 1:0.5 | 1:1 | 1:1.5 | 1:2 |
| Conc. of PEG for 2.85 mM GlucDH2 | 0 | 1.42 mM | 2.85 mM | 4.2 mM | 5.7 mM |
| mol. wt. via GPC (kDa) | 112 | 112-250 | 250-1000 | 1000-2000 | no GPC |
| % mobility (supernatant test) | 100% | 73% | 14.5% | 6.8% | 1.4% |
| Stability in a test element (% residual activity, 1 week, 35° C., 85% rel. hum.) | 72% | 90% | 81% | 119% | 111% |

Example 3

Methods:
In further experiments, NHS-activated PEGs with molecular masses >3,000 g/mol were tested.
Results:
Here, it was found that cross-linking was less efficient than in Example 2. Moreover, cross-linking products obtained with NHS-activated PEG with molecular masses of 10,000 and 20,000 g/mol resulted in very viscous products, which made further processing difficult. Accordingly, PEGs with molecular masses of >3,000 g/mol were found to be less preferred for cross-linking GlucDH2.

Example 4

Figure 3:
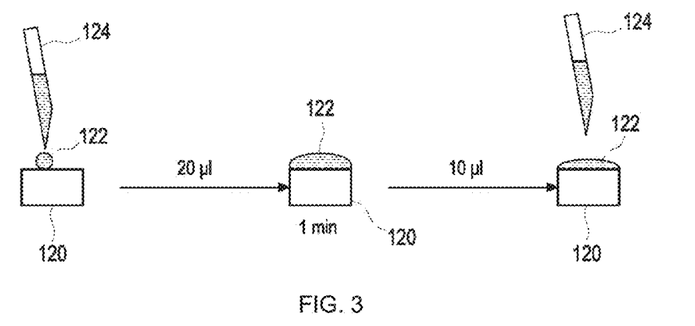
FIG. 3 shows a schematic representation of steps of an exemplary diffusion/immobilization test: 20 μl of buffer is pipetted onto a glucose-detecting test element via a pipette. After 1 minute, 10 µl of a buffer is withdrawn into the pipet and used for further analysis.
Figure 4A:
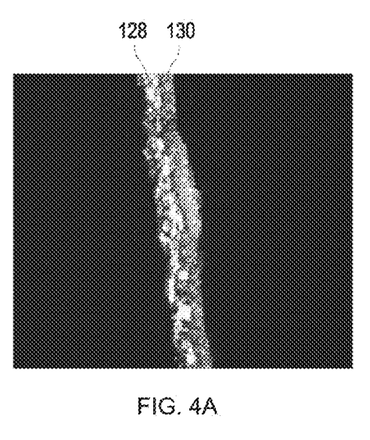
FIGS. 4A-B show fluorescence-microscopic pictures of dry test elements including fluorescently labeled enzyme directly after producing the layers.
Figure 4B:
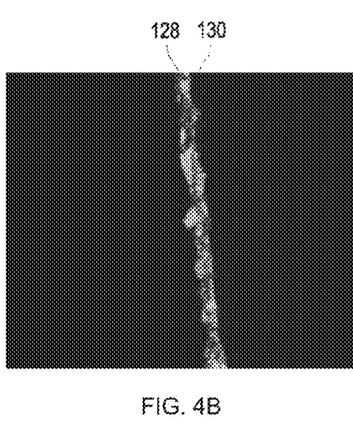
Figure 5A:
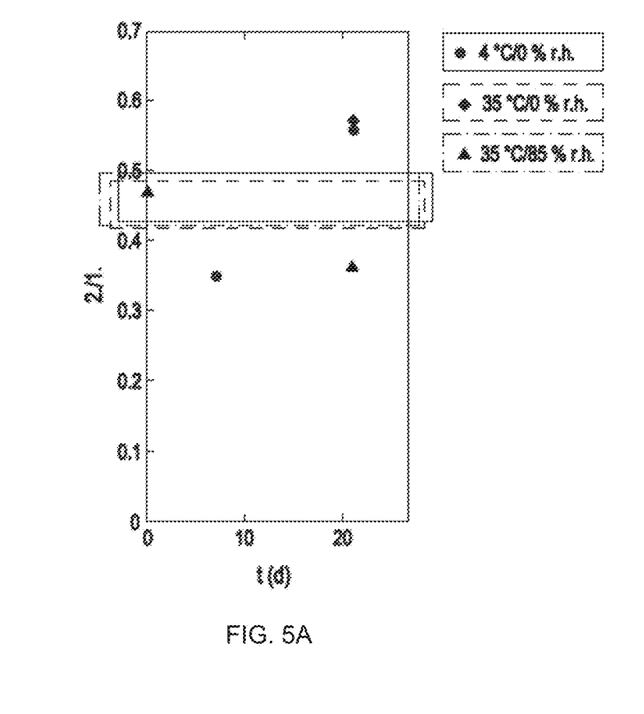
FIGS. 5A-B show a quantitative evaluation of a fluorescence-microscopic analysis of the diffusion of the fluorescent signal between the first and second layer of a test element while stored under various conditions. X-axis: incubation time (days); Y-axis: ratio of amount of enzyme found in the second layer vs. amount of enzyme found in first layer. As above.
Figure 5B:
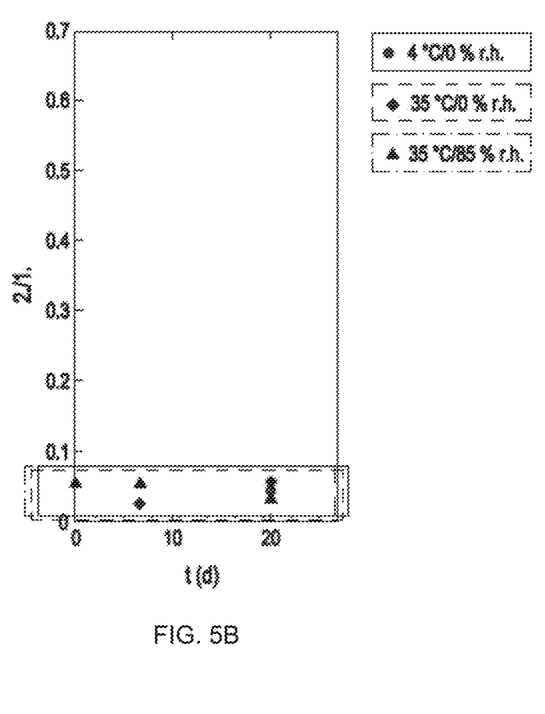

Methods and Results:
For the following experiments, the following standard reaction conditions were used for cross-linking GlucDH2.
To a solution of 2.85 mM GlucDH2 (80 mg/ml protein solution) in 0.2 molar sodium bicarbonate buffer pH 8.3, NHS-PEG in DMSO was added to a concentration of 4.2 mM while stirring at room temperature by slow dropping. The resulting viscous solution was dialyzed 3 times against 0.05 M sodium/potassium phosphate buffer pH 7.0 having 0.2 M NaCl and once against 0.05 M potassium/sodium phosphate buffer pH 7.0. The cross-linking products thus produced were further characterized.
a. Immobilization Test (supernatant test): As a first test for immobilization of the enzyme, 20 µl buffer were pipetted onto a test chemistry including the respective GlucDH2 preparation and were incubated for 1 minute. After this time, 10 µl of the buffer were withdrawn and analyzed for GlucDH2 activity (FIG. 3). The activity diffusing into the buffer is expressed in Table 2 as a percentage of total activity applied. As can be seen from Table 2, the amount of diffusible enzyme decreases drastically with increasing molecular weight of the cross-link products.
b. Diffusion Test (fluorescence microscopy): For this assay, GlucDH2 was chemically coupled to the fluorescent dye Alexa Flour® 647, which can be excited at a wavelength of 650 nm, leading to a fluorescence emission at 668 nm. Fluorescently labeled enzyme was used in the cross-linking reaction as described above and was applied to a first layer of two-layered glucose test elements. The test elements were stored under various conditions for various periods of time, whereafter localization of the enzyme was examined by fluorescence microscopy (see, FIGS. 4A-B and 5A-B). It was found that diffusion of the enzyme into the second layer could essentially be prevented.

Example 5

Methods and Results:
In further experiments, stability of the cross-linked GlucDH2 was examined.

Figure 6A:
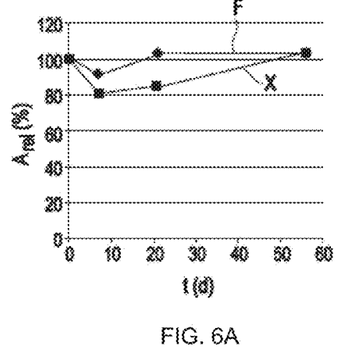
FIGS. 6A-B show stability of GlucDH2 under various storage conditions. F: free enzyme; X: cross-linked enzyme.
Figure 6B:
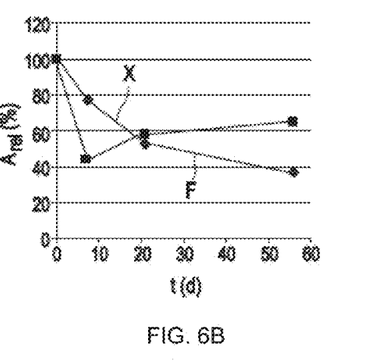
Figure 7A:
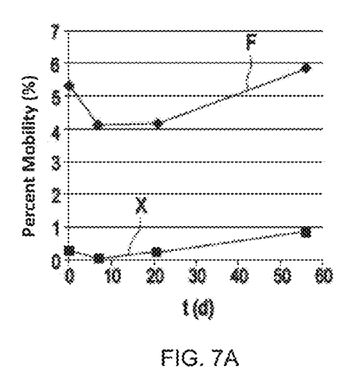
FIGS. 7A-B show mobility of GlucDH2 after storage under dry and warm conditions or moist and warm conditions. F: free GlucDH2; X: cross-linked GlucDH2.
Figure 7B:
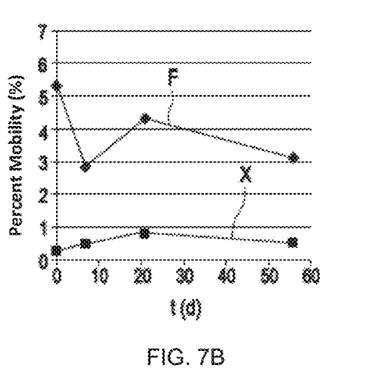

Here, test elements were produced as described above and stored under the conditions indicated in Example 4, which then were examined for remaining activity after several days (see, FIGS. 6A-B). It was found that under dry and warm conditions (e.g., 35° C./0% relative humidity), no significant difference between free enzyme and cross-linked enzyme was found. In contrast, cross-linked enzyme showed a 20% higher residual activity after 55 days under moist and warm conditions (e.g., 35° C./85% relative humidity).
For the aforesaid test elements, the supernatant test (Example 4a) for mobility also was performed. It was found that free GlucDH2 had an average mobility of 3% to 6%, whereas cross-linked GlucDH2 had a mobility of less than 1% under all conditions, indicating immobilization of the enzyme in the first layer of the test elements (see, FIGS. 7A-B).

Example 6

Figure 8:
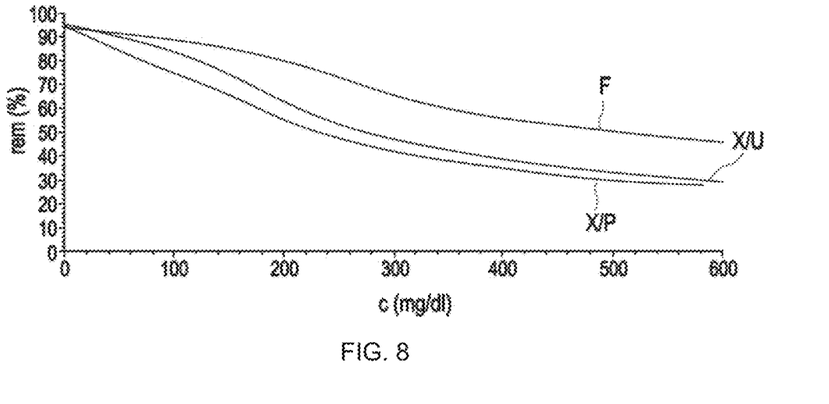
FIG. 8 shows performance of GlucDH2 at various glucose concentrations. In each case, relative remission dependent upon glucose concentration of a glucose-specific test element is indicated. X-axis: glucose concentration in mg/dL; Y-axis: relative remission (%). F: free GlucDH2; X/U: cross-linked GlucDH2, unpurified (having a fraction of free enzyme); and X/P: cross-linked GlucDH2, purified (devoid of free enzyme).

Methods and Results:
To compare kinetics and signal dynamics of free GlucDH2 and cross-linked GlucDH2, test elements including either of the enzyme preparations were tested for kinetic and signal dynamic parameters (FIG. 8). It was found that cross-linking the enzyme does not result in a significant difference. Surprisingly, in colorimetric test strips using cNAD chemistry, diffusion of cNADH was apparently so fast that an increased production of color in the first layer, which is the layer examined photometrically, cannot be observed. In contrast, a different chemistry producing heteropolyblue as a final colored reaction product showed a different behavior. In particular, at glucose concentrations of less than 200 mg/dl, glucose dependence of the resulting signal was much stronger if cross-linked enzyme was used when compared to free enzyme, leading to a significantly improved performance of the system.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

LISTING OF REFERENCE NUMBERS 120 glucose test element
122 buffer
124 pipette
128 first layer of glucose test element
130 second layer of glucose test element

The invention claimed is:

1. A method of cross-linking polypeptide molecules, the method comprising the step of:
combining a cross-linking agent and polypeptide molecules in a solution under conditions suitable for a cross-linking reaction to occur, wherein the cross-linking agent comprises a contiguous chain of at least 40 atoms, wherein the polypeptide molecules are glucose dehydrogenase, and wherein at least 80% of the polypeptide molecules are glucose dehydrogenase.

2. The Method of claim 1, wherein at least 90% of the polypeptide molecules are glucose dehydrogenase.

3. The method of claim 1, wherein the cross-linking agent is an unbranched molecule chemically activated at both ends.

4. The method of claim 1, wherein the cross-linking agent is bis-activated polyethylene glycol.

5. The method of claim 1, wherein the cross-linking agent has a molecular mass selected from the group consisting of 0.6 kDa to 20 kDa, 0.9 kDa to 10 kDa, 1 kDa to 5 kDa, and 3 kDa.

6. The method of claim 1, wherein the polypeptide molecules are present in the solution at an initial concentration selected from the group consisting of 0.1 mM to 5 mM, 0.3 mM to 4 mM, and 1.5 mM to 2.5 mM.

7. The method of claim 1, wherein the molar ratio of cross-linking agent:polypeptide molecules is selected from the group consisting of 0.2:5, 0.5:4, 0.8:3, and 1:2.

8. A preparation comprising cross-linked polypeptide molecules obtained by the method of claim 1.

9. Cross-linked polypeptide molecules, wherein the cross-linked polypeptide molecules are cross-linked by unbranched cross-linking groups comprising at least 40 contiguous atoms, wherein the polypeptide molecules are glucose dehydrogenase.

10. A test chemistry matrix comprising:
a redox cofactor;
an agent capable of eliciting a change in at least one measurable property of an indicator reagent in the presence of redox equivalents;
an indicator reagent; and
the preparation of cross-linked polypeptide molecules obtained by the method of claim 1.

11. A diagnostic test element for determining an analyte concentration in a body fluid sample comprising the test chemistry matrix of claim 10 applied on a surface of a carrier.

12. A method of producing a test chemistry matrix, the method comprising the step of:
admixing a redox cofactor, an agent capable of eliciting a change in at least one measurable property of an indicator reagent in the presence of redox equivalents, an indicator reagent, and the preparation of cross-linked enzyme molecules of claim 8 to produce the test chemistry matrix therefrom.

13. The method of claim 12, wherein two or more of the redox cofactor, the agent capable of eliciting a change in at least one measurable property of an indicator reagent, and the indicator agent are one compound.

* * * * *